US010471222B2

(12) United States Patent
Fink et al.

(10) Patent No.: US 10,471,222 B2
(45) Date of Patent: Nov. 12, 2019

(54) AEROSOLIZATION SYSTEM WITH FLOW RESTRICTOR AND FEEDBACK DEVICE

(71) Applicant: Dance Biopharm Inc., Brisbane, CA (US)

(72) Inventors: Jim Fink, Brisbane, CA (US); Lisa Molloy, Brisbane, CA (US); Ronan MacLoughlin, Craughwell (IE); Claire Lillis, Kingston (IE); Michael Casey, CorrnaMona (IE); John Mullins, Tuam (IE); Kieran Hyland, Salthill (IE); Joe Grehan, Gort (IE)

(73) Assignee: Dance Biopharm Inc., Brisbane, CA (US)

( * ) Notice: Subject to any disclaimer, the term of this patent is extended or adjusted under 35 U.S.C. 154(b) by 1083 days.

(21) Appl. No.: 14/743,763

(22) Filed: Jun. 18, 2015

(65) Prior Publication Data
US 2016/0001018 A1   Jan. 7, 2016

Related U.S. Application Data

(60) Provisional application No. 62/019,791, filed on Jul. 1, 2014.

(51) Int. Cl.
*A61M 15/00* (2006.01)
*A61M 11/00* (2006.01)
*A61M 16/00* (2006.01)

(52) U.S. Cl.
CPC ........ *A61M 15/002* (2014.02); *A61M 11/005* (2013.01); *A61M 15/0021* (2014.02); *A61M 2205/502* (2013.01); *A61M 2206/11* (2013.01)

(58) Field of Classification Search
CPC ............ A61M 15/002; A61M 15/0021; A61M 15/085; A61M 11/005; A61M 2016/0021;
(Continued)

(56) References Cited

U.S. PATENT DOCUMENTS

| 3,789,843 A | 2/1974 | Armstrong et al. |
| 4,564,129 A | 1/1986 | Urban et al. |

(Continued)

FOREIGN PATENT DOCUMENTS

| EP | 2 724 741 A1 | 4/2014 |
| RU | 2383358 C2 | 3/2010 |

(Continued)

OTHER PUBLICATIONS

Liu, F-Y, "Pulmonary Delivery of Free Liposomal Insulin," Pharmaceutical Research, Kluwer Academic Publishers, New York, NY, vol. 10, No. 2, Feb. 1, 1993, 5 pages.
(Continued)

*Primary Examiner* — Kendra D Carter
*Assistant Examiner* — Jonathan S Paciorek
(74) *Attorney, Agent, or Firm* — Kilpatrick Townsend & Stockton LLP

(57) ABSTRACT

In one aspect, embodiments of the present invention provide an aerosolization device for ensuring proper delivery of an aerosolized medication to a user's respiratory system. The aerosolization device may include a conduit, an aerosol generator, a restrictor disposed within the conduit, and an indicator mechanism. The conduit may include a mouthpiece end by which a user may cause inspiratory flow through the conduit. The aerosol generator may include a vibratable mesh. The restrictor may define a plurality of apertures disposed along an outer periphery of the restrictor configured to provide an increase in pressure differential that varies with an inspiratory flow rate within the conduit and to provide a relatively laminar flow downstream of the restrictor compared to upstream of the restrictor. The indicator mechanism may indicate to a user a state of a parameter of the inspiratory flow relative to a predefined desired range.

14 Claims, 14 Drawing Sheets

(58) Field of Classification Search
CPC .... A61M 2016/0027; A61M 2016/003; A61M 2205/3331; A61M 2205/502; A61M 2205/52; A61M 2205/581; A61M 2205/582; A61M 2205/584; A61M 2205/6018; A61M 2205/6054; A61M 2205/8206; A61M 2206/11

See application file for complete search history.

(56) References Cited

U.S. PATENT DOCUMENTS

| | | | |
|---|---|---|---|
| 5,060,642 | A | 10/1991 | Gilman |
| 5,134,993 | A | 8/1992 | Van Der Linden et al. |
| 5,164,740 | A | 11/1992 | Ivri |
| 5,320,094 | A | 6/1994 | Laube et al. |
| 5,333,106 | A | 7/1994 | Lanpher et al. |
| 5,347,998 | A | 9/1994 | Hodson et al. |
| 5,363,842 | A | 11/1994 | Mishelevich et al. |
| 5,364,838 | A | 11/1994 | Rubsamen |
| 5,474,059 | A * | 12/1995 | Cooper .................. A61M 11/06 128/200.22 |
| 5,479,920 | A | 1/1996 | Piper et al. |
| 5,515,842 | A | 5/1996 | Ramseyer et al. |
| 5,586,550 | A | 12/1996 | Ivri et al. |
| 5,655,520 | A | 8/1997 | Howe et al. |
| 5,672,581 | A | 9/1997 | Rubsamen et al. |
| 5,743,250 | A * | 4/1998 | Gonda .................. A61K 9/007 128/200.14 |
| 5,758,637 | A | 6/1998 | Ivri et al. |
| 5,759,101 | A | 6/1998 | Von Kohorn |
| 5,884,620 | A | 3/1999 | Gonda et al. |
| 5,915,378 | A | 6/1999 | Lloyd et al. |
| 5,938,117 | A | 8/1999 | Ivri |
| 5,941,240 | A | 8/1999 | Gonda et al. |
| 5,957,124 | A | 9/1999 | Lloyd et al. |
| 6,014,970 | A | 1/2000 | Ivri et al. |
| 6,085,740 | A | 7/2000 | Ivri et al. |
| 6,085,753 | A | 7/2000 | Gonda et al. |
| 6,089,260 | A | 7/2000 | Jaworski et al. |
| 6,098,615 | A | 8/2000 | Lloyd et al. |
| 6,109,261 | A | 8/2000 | Clarke et al. |
| 6,131,567 | A | 10/2000 | Gonda et al. |
| 6,205,999 | B1 | 3/2001 | Ivri et al. |
| 6,312,665 | B1 | 11/2001 | Modi |
| 6,408,854 | B1 | 6/2002 | Gonda et al. |
| 6,427,682 | B1 | 8/2002 | Klimowicz et al. |
| 6,467,476 | B1 | 10/2002 | Ivri et al. |
| 6,534,701 | B2 | 3/2003 | Isozaki |
| 6,540,153 | B1 | 4/2003 | Ivri |
| 6,540,154 | B1 | 4/2003 | Ivri |
| 6,543,701 | B1 | 4/2003 | Ho |
| 6,629,646 | B1 | 10/2003 | Ivri |
| 6,640,804 | B2 | 11/2003 | Ivri et al. |
| 6,647,987 | B2 | 11/2003 | Gonda et al. |
| 6,655,379 | B2 * | 12/2003 | Clark .................. A61K 9/0073 128/203.12 |
| 6,681,762 | B1 | 1/2004 | Scheuch et al. |
| 6,688,304 | B2 | 2/2004 | Gonda et al. |
| 6,755,189 | B2 | 6/2004 | Ivri et al. |
| 6,814,071 | B2 | 11/2004 | Klimowicz et al. |
| 6,904,908 | B2 * | 6/2005 | Bruce .................. A61M 15/0086 128/200.23 |
| 6,921,020 | B2 | 7/2005 | Ivri |
| 6,926,208 | B2 | 8/2005 | Ivri |
| 6,978,941 | B2 | 12/2005 | Litherland et al. |
| 7,028,686 | B2 | 4/2006 | Gonda et al. |
| 7,032,590 | B2 | 4/2006 | Loeffler et al. |
| 7,040,549 | B2 | 5/2006 | Ivri et al. |
| 7,066,398 | B2 | 6/2006 | Borland et al. |
| 7,083,112 | B2 | 8/2006 | Ivri |
| 7,100,600 | B2 | 9/2006 | Loeffler et al. |
| 7,108,197 | B2 | 10/2006 | Ivri |
| 7,131,440 | B2 | 11/2006 | Sonntag |
| 7,174,888 | B2 | 2/2007 | Ivri et al. |
| 7,185,651 | B2 | 3/2007 | Alston et al. |
| 7,195,011 | B2 | 3/2007 | Loeffler et al. |
| 7,219,664 | B2 | 5/2007 | Ruckdeschel et al. |
| 7,364,571 | B2 | 4/2008 | Schinazi et al. |
| 7,448,375 | B2 | 11/2008 | Gonda et al. |
| 7,451,760 | B2 | 11/2008 | Denyer et al. |
| 7,600,512 | B2 | 10/2009 | Lee et al. |
| 7,628,339 | B2 | 12/2009 | Ivri et al. |
| 7,683,029 | B2 | 3/2010 | Hindle et al. |
| 7,748,382 | B2 | 7/2010 | Denyer et al. |
| 7,819,115 | B2 | 10/2010 | Sexton et al. |
| 7,891,358 | B2 | 2/2011 | Kolb et al. |
| 7,913,688 | B2 | 3/2011 | Cross et al. |
| 8,082,918 | B2 | 12/2011 | Jansen et al. |
| 8,950,394 | B2 | 2/2015 | Patton et al. |
| 9,004,061 | B2 | 4/2015 | Patton et al. |
| 2001/0037805 | A1 | 11/2001 | Gonda et al. |
| 2001/0039948 | A1 | 11/2001 | Sexton et al. |
| 2003/0019493 | A1 | 1/2003 | Narayan et al. |
| 2003/0047620 | A1 | 3/2003 | Litherland et al. |
| 2004/0134494 | A1 | 7/2004 | Papania et al. |
| 2005/0011514 | A1 * | 1/2005 | Power ............... A61M 15/0085 128/200.14 |
| 2006/0239930 | A1 | 10/2006 | Lamche et al. |
| 2007/0113841 | A1 | 5/2007 | Fuchs |
| 2007/0144514 | A1 * | 6/2007 | Yeates ............... A61M 15/0086 128/203.15 |
| 2007/0163572 | A1 | 7/2007 | Addington et al. |
| 2008/0029083 | A1 | 2/2008 | Masada et al. |
| 2008/0060641 | A1 | 3/2008 | Smith et al. |
| 2008/0233053 | A1 | 9/2008 | Gross et al. |
| 2009/0056708 | A1 | 3/2009 | Stenzler et al. |
| 2009/0157037 | A1 | 6/2009 | Iyer et al. |
| 2009/0241948 | A1 * | 10/2009 | Clancy ............... A61B 17/3474 128/203.14 |
| 2009/0301472 | A1 | 12/2009 | Kim et al. |
| 2010/0075001 | A1 | 3/2010 | Succar et al. |
| 2010/0078015 | A1 | 4/2010 | Imran |
| 2010/0154794 | A1 | 6/2010 | Valentin |
| 2010/0319686 | A1 | 12/2010 | Schennum |
| 2011/0114089 | A1 | 5/2011 | Andersen et al. |
| 2011/0168172 | A1 | 7/2011 | Patton et al. |
| 2011/0226242 | A1 | 9/2011 | Von Hollen et al. |
| 2012/0041381 | A1 | 2/2012 | Raj et al. |
| 2012/0048268 | A1 | 3/2012 | Hyun et al. |
| 2013/0004645 | A1 | 1/2013 | Paglino |
| 2013/0269684 | A1 | 10/2013 | Patton |
| 2013/0269694 | A1 | 10/2013 | Patton et al. |
| 2014/0041653 | A1 | 2/2014 | Patton et al. |
| 2014/0254128 | A1 | 9/2014 | Ikeda et al. |
| 2014/0318533 | A1 | 10/2014 | Patton et al. |
| 2015/0048119 | A1 | 2/2015 | Boehm et al. |

FOREIGN PATENT DOCUMENTS

| | | |
|---|---|---|
| WO | 1992/11050 A1 | 7/1992 |
| WO | 1998/22290 | 5/1998 |
| WO | 2003/030829 | 4/2003 |
| WO | 2004/028608 | 4/2004 |
| WO | 2006/062449 | 6/2006 |
| WO | 2007/047948 | 4/2007 |
| WO | 2007047948 | 4/2007 |
| WO | 2012/026963 A2 | 3/2012 |
| WO | 2013/098334 A1 | 7/2013 |

OTHER PUBLICATIONS

International Search Report and Written Opinion of PCT/US2011/020926 dated Mar. 14, 2011, 11 pages.

International Search Report and Written Opinion of PCT/US2011/020925 dated Mar. 14, 2011, 7 pages.

International Search Report and Written Opinion of PCT/US2013/034359 dated Jun. 28, 2013, 35 pages.

European Search Report of EP 11733287 dated Jul. 12, 2013, 12 pages.

International Patent Application No. PCT/US2015/037505, "International Search Report and Written Opinion" dated Sep. 29, 2015, 10 pages.

(56) References Cited

OTHER PUBLICATIONS

International Patent Application No. PCT/US2015/037505, "International Preliminary Report on Patentability" dated Jan. 12, 2017, 8 pages.
Clark; 2012 "Understanding Penetration Index Measurements and Regional Lung Targeting" Journal of Aerosol Medicine and Pulmonary Drug Delivery, 25(4), 179-187.
EP Application No. 15816007.7 received and Extended European Search Report dated Jan. 26, 2018, 8 pages.
Kikoin, et al., "Physics for $8^{th}$ Grade", Textbook, $4^{th}$ Edition, revied, M. Prosveshcheniye, 1973, 256 pages, p. 236, the last paragraph, where it is stated that the pressure of a flowing liquid is larger in those flow cross-sections in which its flow rate is less.
Savelyev I.V., "Physics: A General Course", vol. 1, mechanics Molecular Physics: Textbook, $2^{nd}$ Edition, revised, M.: Nauka, Chief editorial board of physical and mathematical literature, 1982, 432 pages, where formula (76.1) is given on p. 255, from which it follows that the reductions of a flow rate, when the properties of the flow and the size of the cross-section are preserved, decreases the value of the Reynolds criterion. It is also stated on p. 255, the sixth paragraph, lines 1-3, that a laminar flow is observed with small values of the Reynolds number.

\* cited by examiner

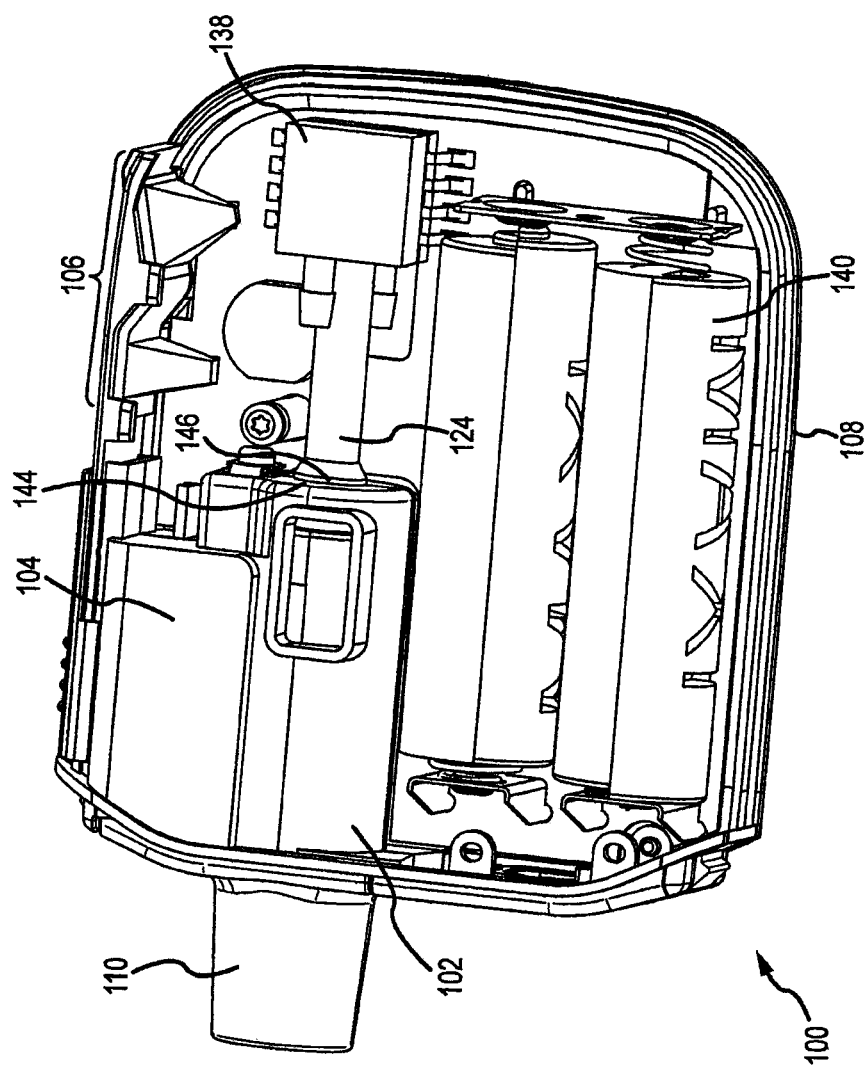

AEROSOLIZATION SYSTEM WITH FLOW RESTRICTOR AND FEEDBACK DEVICE

CROSS REFERENCE TO RELATED APPLICATIONS

This application is related to U.S. Provisional Application No. 62/019,791, filed on Jul. 1, 2014, entitled "AEROSOLIZATION SYSTEM WITH FLOW RESTRICTOR AND FEEDBACK DEVICE," the entire disclosure of which is hereby incorporated by reference, for all purposes, as if fully set forth herein.

BACKGROUND OF THE INVENTION

Aerosolization systems provide effective delivery for a variety of medicaments, such as insulin and asthma medications. Such systems deliver the medicaments directly to a user's respiratory system by aerosolizing a desired dose of the medicament in liquid form. The user then inhales the aerosolized medicament directly into the respiratory system, enabling faster treatment of various medical conditions.

Delivery of accurate and consistent metered doses of aerosolized medicament to a user is very important. Current aerosolization systems often provide inconsistent doses by allowing some of the medicament to remain in a reservoir in liquid form after the aerosolization process is completed. Additionally, the aerosolized medicament is often delivered with too great or too little force for substantially all of the metered dose to properly enter the user's respiratory system. A further problem of current aerosolization systems is a tendency for the medicament to become contaminated by the user or other sources. Contamination of the medicament is particularly problematic since some or all of the contaminated medicament is thereafter delivered directly to the user's respiratory system after aerosolization. Embodiments of the invention may provide solutions to these and other problems.

BRIEF SUMMARY OF THE INVENTION

In one embodiment, an aerosolization device for ensuring proper delivery of an aerosolized medication to a user's respiratory system is provided. The aerosolization device may include a conduit, an aerosol generator in communication with the conduit, a restrictor disposed within the conduit, and an indicator mechanism. The conduit may include a mouthpiece end by which a user may cause an inspiratory flow through the conduit. The aerosol generator may include a vibratable mesh. The restrictor may define a plurality of apertures disposed along an outer periphery of the restrictor. The plurality of apertures may be configured to provide an increase in pressure differential that varies with an inspiratory flow rate within the conduit and to provide a relatively laminar flow downstream of the restrictor compared to upstream of the restrictor. The indicator mechanism may indicate to a user a state of a parameter of the inspiratory flow relative to a predefined desired range.

In another embodiment, a different aerosolization device for ensuring proper delivery of an aerosolized medication to a user's respiratory system is provided. The aerosolization device may include a conduit, an aerosol generator in communication with the conduit, and a restrictor disposed within the conduit. The conduit may have a mouthpiece end by which a user may cause an inspiratory flow through the conduit. The aerosol generator may include a vibratable mesh. The restrictor may define a plurality of apertures disposed along an outer periphery of the restrictor. The plurality of apertures may be configured to provide an increase in pressure differential that varies with an inspiratory flow rate within the conduit and to provide a relatively laminar flow downstream of the restrictor compared to upstream of the restrictor. The vibratable mesh may produce a plume of aerosolized medicament within the relatively laminar flow when the inspiratory flow rate is within an operating range of the aerosol device.

In another embodiment, a method of delivering an aerosolized medication to a user's respiratory system is provided. The method may include sensing a state of a flow parameter of an inspiratory flow within a conduit. The conduit may have a mouthpiece end by which a user may cause the inspiratory flow within the conduit. The method may also include vibrating a mesh of an aerosol generator in communication with the conduit to aerosolize a volume of a liquid medicament to produce a plume of aerosolized medicament within the conduit when the state of the flow parameter is within a predefined desired range. The plume of aerosolized medicament may be provided within a relatively laminar flow produced by a restrictor disposed within the conduit upstream of the plume of aerosolized medicament. The restrictor may define a plurality of apertures disposed around an outer periphery of the restrictor. The plume of aerosolized medicament may be carried by the relatively laminar flow toward the mouthpiece end of the conduit. The method may further include providing an indication using an indicator mechanism of the state of the flow parameter relative to the predefined desired range.

BRIEF DESCRIPTION OF THE DRAWINGS

The present invention is described in conjunction with the appended figures:

FIG. 1A depicts an interior of an aerosolization device according to embodiments of the invention;

Figure 1B:
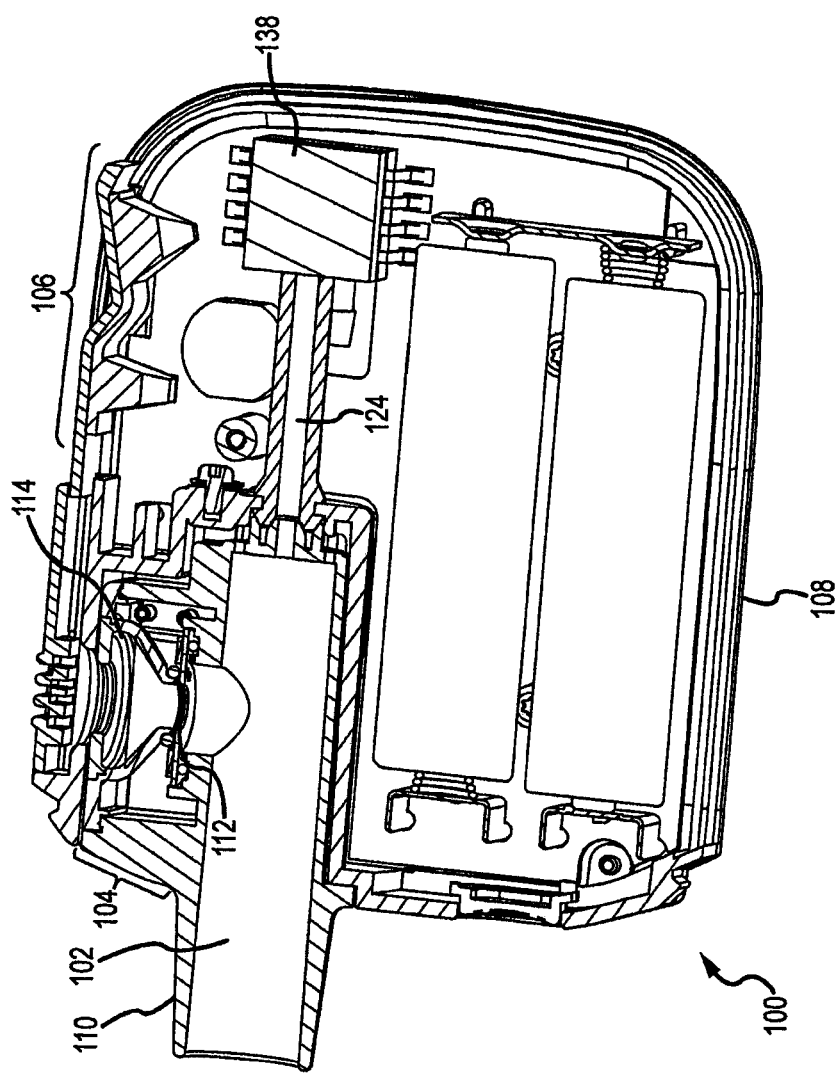
FIG. 1B shows a cross section of FIG. 1A according to embodiments of the invention.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION OF THE INVENTION

The ensuing description provides exemplary embodiments only, and is not intended to limit the scope, applicability or configuration of the invention. Rather, the ensuing description of exemplary embodiments will provide those skilled in the art with an enabling description for implementing various embodiments of the invention. It will be understood that various changes may be made in the function and arrangement of elements without departing from the spirit and scope of the invention as set forth in the appended claims. For example, any detail discussed with regard to one embodiment may or may not be present in variations of that embodiment, and/or in other embodiments discussed herein.

Embodiments of an aerosolization device for assisting in proper delivery of an aerosolized medication to a user's respiratory system are described herein. In many embodiments, liquid medicament may be provided to an aerosolization device in a metered dose. The liquid medicament may be dispensed to an aerosol generator. In some embodiments, the liquid medicament may be provided via a chamber or reservoir that funnels the liquid medicament into the aerosol generator where the liquid medicament is aerosolized for delivery into a user's respiratory system. In other embodiments, a separate container holding the liquid medicament may couple with the aerosolization device to provide the liquid medicament thereto.

In some embodiments, an aerosolization device may include a conduit, an aerosol generator in communication with the conduit, a restrictor plate disposed within the conduit, and an indicator mechanism coupled with the conduit. In many embodiments, some or all of these components are disposed within a housing. In some embodiments, the conduit and/or the aerosol generator may be removably coupled with or received within the housing. By providing a removable conduit and/or aerosol generator, the aerosolization device may be easily cleaned and dried, thus preventing contamination and buildup of pathogens and/or other contaminants.

In some embodiments, the conduit may include a mouthpiece end by which a user may cause an inspiratory flow through the conduit. A user may inhale through the mouthpiece to create the inspiratory flow of air that may transport an aerosolized medicament to the user. In some embodiments, the mouthpiece end of the conduit may deliver the aerosolized medicament to the user at an angle relative to a horizontal plane. Such a delivery angle may be selected based on the dosage and type of medicament to be delivered to the user's respiratory to ensure that a substantial portion of the aerosolized medicament is delivered to the respiratory system without becoming stuck in the user's mouth, throat, and/or other area.

In many embodiments, a sensor is used to determine when a parameter of the inspiratory flow is within a predefined desired or operating range of the aerosolization device and/or the aerosol generator. For example, a flow sensor or pressure transducer may be used to determine a flow rate or pressure differential within the conduit. Other types of sensors and flow parameters may also be employed/measured. For example, the flow parameter can be an inspiratory flow rate, inspiratory pressure, inspiration time, and the like detected by a flow sensor, timer, pressure transducer, or other sensing mechanism. A processing unit coupled with the sensor may compare the sensed value to a stored desired range. In some embodiments, the desired range of a flow parameter for a particular medicament delivery may correspond to the operating range of the aerosol generator. In other embodiments, the desired range of a flow parameter may be narrower or broader than the operating range of the aerosol generator.

In some embodiments, the aerosol generator may include a vibratable mesh. When the parameter of the inspiratory flow is within the desired or operating range, the vibratable mesh may be vibrated for an operating period sufficient to aerosolize substantially all of any liquid medicament disposed on a top of the vibratable mesh. The vibratable mesh may be domed shaped and be vibrated by an annular piezoelectric element (not shown) or other electro-mechanical resonating device that circumscribes the vibratable mesh. The vibratable mesh is vibrated when one or more flow parameters are within an operating range of the aerosol generator. For example, a flow sensor and/or pressure transducer in communication with the conduit may detect that an inspiratory flow rate and/or a pressure differential within the conduit is within an operating range of the aerosol generator. A processor may control a circuit to provide an electric current to the piezoelectric element to vibrate the mesh. Typically, the vibratable mesh will be vibrated at a frequency in the range from about 50 kHz to about 150 kHz to aerosolize the dose of liquid medicament.

In many embodiments, the inhaled air may pass through a restrictor array within the conduit. In one embodiment, the restrictor array may be a restrictor plate that has a plurality of apertures passing therethrough. As air passes through the apertures, the apertures provide an increase in pressure differential that varies according to the inspiratory flow rate within the conduit. The apertures also provide a relatively laminar flow downstream of the restrictor plate compared to upstream of the restrictor plate. In many embodiments, the apertures are disposed along an outer periphery of the restrictor plate. In some embodiments, the vibratable mesh may be located downstream of the restrictor plate or other restrictor array and produce a plume of aerosolized medicament within the relatively laminar flow produced by the restrictor array. In some embodiments, the restrictor array may include multiple restrictor plates in series.

The indicator mechanism may indicate to a user a state of a parameter of the inspiratory flow relative to a predefined desired range. In some embodiments, the indicator mechanism may indicate to the user a state of the aerosolization device in the alternative or in addition to indicating a state of a parameter of the flow. For example, the indicator may be a light, analog/digital display or readout, speaker, vibration-generating device, and/or other feature that alerts a user as to the state of the parameter. In some embodiments, the state of the parameter can be an inspiratory flow rate, inspiratory pressure, inspiration time, and the like detected by a flow sensor, timer, pressure transducer, or other sensing mechanism. The indictor may inform the user if they are within or outside of the desired range for the parameter.

In some embodiments, an 'end of dose' indication can be provided to a user when an entire dose of the medicament has been aerosolized. Such an indication may be provided upon a sensor, such as a load or flow sensor, detects that substantially all of the medicament has been aerosolized. Another indication may also be provided to the user informing them of when the liquid medicament is actually being aerosolized by the activated vibratable mesh. Such indications of a state of the flow parameter and/or state of the aerosolization device can be provided by the indicator mechanism described above, such as by providing a distinguishable indication from the indication of the state of the flow parameter. For example, the state of the flow parameter may be indicated by a green light and the indication of the end of dose may be provided by a blue light. In other embodiments, the end of dose indication and/or the aerosolization indication may be provided by one or more separate indicator mechanisms.

In some embodiments, the indicator mechanism may be used direct a user in how to properly inhale and thereby ensure proper delivery of the medicament to the user's respiratory system. To do so, the indicator mechanism may alert the user when a parameter, such as an inspiratory flow rate within the conduit, is within a predefined desired range. The aerosol generator may be configured to aerosolize the liquid medicament when the inspiratory flow is within the redefined flow rate range. For example, the predefined desired range of the inspiratory flow rate within the conduit may be between about 5 and 14 liters per minute (L/min). An indication as described above, such as a light or sound emitted by a speaker, may be produced to alert the user that the user's inhalation is maintaining the inspiratory flow rate within the desired range, and thus when the aerosol generator is active.

In some embodiments, a first indication may be provided with the parameter is within the desired range and a second indication may be provided when the parameter is outside of the desired range. For example, the first indication may include a light being turned on or a sound, such as a beep, being emitted. The second indication may include a light being turned off or a previous continuously emitted sound ceasing. Other indications may include emitting a different color of light or different frequency of sound than the first indication to indicate a change in state of a parameter. In some embodiments, the second indication can alert a user whether the state of the parameter is higher or lower than the desired range. For example, a flashing light may be emitted with a relatively long period between flashes to alert the user when the state of the parameter is lower than the desired range and a flashing light having a relatively short period between flashes may be emitted to alert the user that the state of the parameter is higher than the desired range. Similar uses of vibrations and sounds may be used in conjunction with, or in alternative to, light indicators.

In some embodiments indicating to the user the state of the parameter of the inspiratory flow relative to the predefined desired range may include the indicator mechanism providing a first indication when the parameter of the inspiratory flow is within the predefined desired range, the indicator mechanism providing a second indication when the parameter of the inspiratory flow is within a predefined secondary range (i.e., potentially an acceptable, but less than optimum, range), and the indicator mechanism providing a third indication when the parameter of the inspiratory flow is outside of both the predefined desired range and the predefined secondary range.

In some embodiments, the aerosolization device may further include an input device for receiving and setting the predefined desired range of the parameter of the inspiratory flow. For example, the input device may include a barcode scanner, radio frequency identification (RFID) reader, keyboard, or any other input device that can receive an input from the user regarding one or more parameters of the inspiratory flow, such as a desired flow rate, inspiratory pressure, or inspiration time. In some embodiments, the desired flow rate may be visually or otherwise encoded on the medicament delivery container, and read by the aerosolization device therefrom.

In some embodiments, the parameter of the inspiratory flow may include the inspiratory flow rate within the conduit. The predefined desired range of the inspiratory flow rate may be between about 5 and 14 liters per minute (L/min). In some embodiments, the parameter of the inspiratory flow may include the inspiration time. The predefined desired range of the inspiration time may be between about 5 and 26 seconds. In some embodiments, multiple parameters may be measured and referred to. For example, in one embodiment, a certain amount of inspiration time of a minimum inspiratory flow may be necessary.

In some embodiments, the aerosolization system may include electronic elements including, but not limited to, a processing element and a memory unit. The processing element may be used to control the actuation of the aerosol generator, indicator mechanisms, and input devices, as well as any sensors such as flow sensors and pressure transducers. The memory unit may be configured to store settings and ranges set by the input device for the parameters of the indicator mechanism and/or aerosol generator. The memory unit may also be configured to store data related to past aerosolization sessions, as well as information provided by medicament delivery vessels attached thereto.

Turning now to the drawings, FIGS. 1A and 1B illustrate an aerosolization device 100, in accordance with various embodiments of the invention. Aerosolization device 100 includes a conduit 102 and an aerosol generator 104 in communication with the conduit 102. The aerosolization device 100 may also include one or more indicator mechanisms 106, shown here as indicator lights. The one or more indicator mechanisms may be coupled with the a housing 108, or some other portion of device 100. Conduit 102 and aerosol generator 104 may also optionally be coupled with housing 108.

In some embodiments, conduit 102 may include a mouthpiece end 110 through which a user may inhale to produce an inspiratory flow to deliver aerosolized medicament to the user's respiratory system. As seen in FIG. 1B, the aerosol generator 104 may include a vibratable mesh 112. Liquid medicament can be dispensed onto the vibratable mesh 112, either directly from a vial of liquid medicament or indirectly by being funneled onto the vibratable mesh 112 by tapered walls of a fluid receiving chamber 114. In many embodiments, the vibratable mesh 112 is vibrated via a mechanism controlled by a processor to aerosolize a volume of liquid medicament when a flow rate of the inspiratory flow is within an operating range of the aerosol generator 104. When vibrated, the vibratable mesh 112 operates to produce a plume of aerosolized medicament within the conduit 102 such that the aerosolized conduit can be inhaled into the user's lungs.

Exemplary aerosol generators that can be used are also described in U.S. Pat. Nos. 5,164,740; 6,629,646; 6,926,208; 7,108,197; 5,938,117; 6,540,153; 6,540,154; 7,040,549; 6,921,020; 7,083,112; 7,628,339; 5,586,550; 5,758,637; 6,085,740; 6,467,476; 6,640,804; 7,174,888; 6,014,970; 6,205,999; 6,755,189; 6,427,682; 6,814,071; 7,066,398; 6,978,941; 7,100,600; 7,032,590; 7,195,011, incorporated herein by reference. These references describe exemplary aerosol generators, ways to manufacture such aerosol generators and ways to supply liquid to aerosol generators, and are incorporated by reference for at least these features.

In some embodiments, the one or more indicator mechanisms 106 may include lights, such as LEDs. Indicator mechanisms 106 may also include speakers/or and vibration generating mechanisms to direct users as to a state of the aerosolization device. For example, indicator mechanisms 106 can be used to direct a user when the aerosolization device 100 is ready for use. Indicator mechanisms 106 may also indicate a state of a parameter of the inspiratory flow created by the user. For example, the indicator mechanisms 106 may instruct a user to alter an inhalation rate to increase or decrease a flow rate within the conduit 102 to ensure proper delivery of the aerosolized medicament and/or to ensure that the flow rate is within the operating range of the aerosol generator 104 such that the vibratable mesh 112 aerosolizes the liquid medicament. Indicator mechanisms 106 may also be used to indicate to a user when substantially all of a dose of liquid medicament has been aerosolized and/or inhaled. Additional sensors may be required in order to provide the functionality described above.

In some embodiments, the aerosolization device 100 include a processing unit or integrated circuit (IC) 138 that controls the function of or runs computer code to control other electronic components of the aerosolization device 100. Aerosolization device 100, including IC 138, may be powered by batteries 140 that are coupled with IC 138. IC 138 may be electrically coupled with electronic components, such as any sensors, indicating mechanisms 106 and/or a piezoelectric element of aerosol generator 104. IC 138 can control the actuation of the indicator mechanisms and/or the aerosol generator 104 based on information received from any sensors, such as flow sensors or pressure transducers in fluid communication with the conduit 102. In some embodiments, IC 138 may be electrically coupled with the conduit 102 and/or the aerosol generator 104 using a plug 124. The conduit 102 and/or aerosol generator 104 may be removable from housing 108. The conduit 102 and/or aerosol generator 104 may be inserted into housing 108 and interfaced with plug 124 to supply power to and control actuation of the aerosol generator 104 based on measurements from sensors in fluid communication with conduit 102. For example plug 124 may have a male connector 144 that interfaces with a female connector 146 on conduit 102. In some embodiments, plug 124 may include a female connector that interfaces with a male connector on conduit 102.

Figure 2:
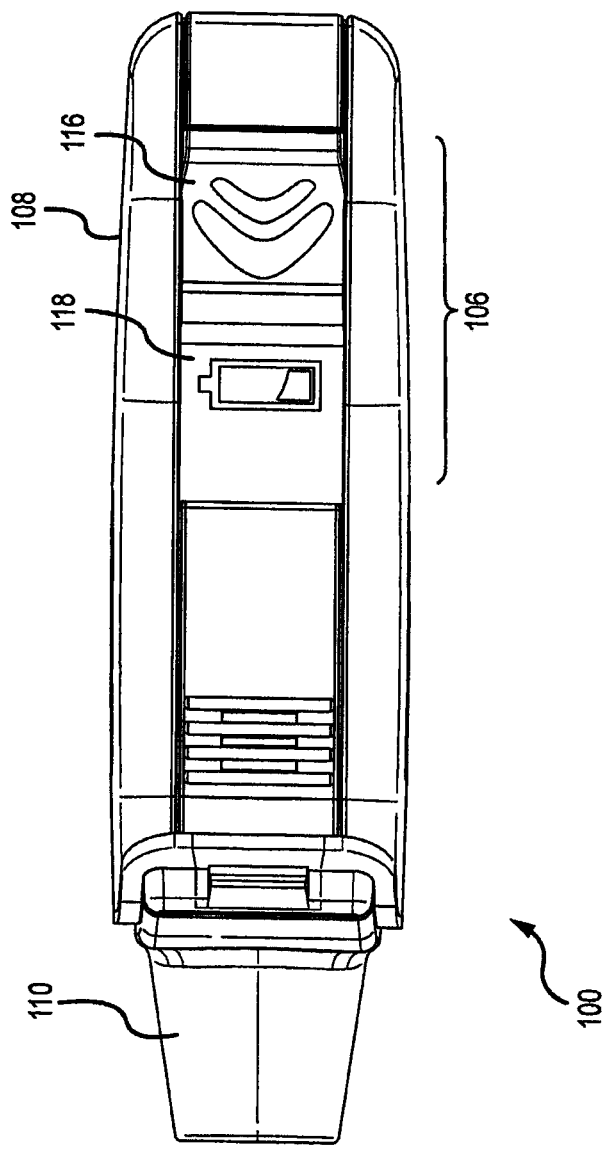
FIG. 2 depicts a front of the aerosolization device of FIG. 1A according to embodiments of the invention.

FIG. 2 shows a top view of aerosolization device 100 and indicator mechanisms 106 according to embodiments of the invention. In some embodiments, indicator mechanisms 106 can include a breathing indicator 116 and a battery indicator 118. Breathing indicator 116 can direct a user when and how to breath to maximize delivery of the aerosolized medicament to the user's lungs. In some embodiments, breathing indicator 116 can include multiple indicators, such as various colored LEDs, to provide the user more detailed guidance. Breathing indicator 116 may be in the shape of a chevron that includes 3 colors of LEDs.

In some embodiments, optimal pulmonary delivery of medicaments such as liquid insulin occurs at specified flow rates and inspiratory times. For example, an optimal flow rate may be between about 5 and 14 L/min, or more often between about 7 and 14 L/min. Flow rates that are too high or too low can result in losses in the amount of aerosolized medicament delivered to the proper locations of a user's respiratory system. An optimal inspiratory time may be between 6 and 24 seconds. Breathing indicator 116 can be used to direct a user to maintain an inhalation within these parameters.

In one embodiment, a light, such as a steady green light emitted from an LED, will be produced using breathing indicator 116 to instruct a user that flow within the aerosolization device 100 is within the operating range of the aerosolization device 100 to aerosolize a dose of medicament. As a user inhales at the mouthpiece end 110 of the conduit 102, the inhalation flow rate is detected by a flow sensor or a pressure transducer that can convert a pressure differential within the conduit 102 into a flow rate. The detection of an inhalation having proper flow parameters results in activation of the aerosol generator 104 to produce aerosolized medicament particles into the conduit 102. The light from breathing indicator 116 may be slowly flashed to indicate that the user is breathing too slowly (i.e., causing a low flow rate) as compared to the operating range, should aspiratory conditions change. For example, a flashing green light may be emitted having a period of between about 500 and 1000 milliseconds (ms) and a frequency of about 1.25 hertz (Hz) to indicate that the aerosolization device 100 is activated during a time with little or no air flow. The light may be flashed quickly to direct the user that they are breathing too quickly (i.e., causing a high flow rate). For example, a flashing green light may be emitted from the breathing indicator 116 having a period of between about 50 and 250 ms and a frequency of about 6.25 Hz when the flow rate is excessive. The aerosol generator 104 may be configured to not aerosolize any medicament when the flow rate is too high or too low.

The breathing indicator 116 may produce a different colored light as an "end of dose" indictor to indicate that substantially all of the dose of medicament has been delivered. For example, a blue light may be emitted for a period of time, such as between about 1 and 10 seconds to alert the user that substantially all of the dose has been aerosolized and inhaled. Delivery of the 'entire' dose may be predefined as when at least about 95% of the dose is delivered, more preferably 98% and most preferably when more than 99% of the dose is aerosolized. To receive the dose, the user may take several inhalations or a single inhalation depending on the volume of liquid drug to be delivered and the user's breathing capacity. Each inhalation may be monitored by the device, with feedback provided to the user via indicator 116, to insure proper delivery to the lungs. In some embodiments, the operation of the end of dose indicator may be delayed for a period, such as up to about 5 seconds after substantially all of the dose has been delivered, thus providing a "chaser" of air into the lungs. This chaser may serve to clear the upper airway and maximize the amount of the dose that is transported to the user's lungs.

In embodiments where the conduit 102 and/or aerosol generator 104 are removable from housing 108, a light may be emitted to instruct a user that one or both of the conduit 102 and the aerosol generator are not completely seated, coupled together, and/or engaged within the housing 108. It will also be appreciated that other shapes and numbers of lights may be used in breathing indicator 116. Breathing indicator 116 may also use different numbers or types of lighting elements, colors of light, intensities of light, flashes of light having different periods, vibration patterns, sounds, and/or any combination of such indications to direct a user on how to properly inhale using the aerosolization device 100. Indicator mechanisms 106 may also be used to provide other indications related to the aerosolization device 100.

In some embodiments, the battery indicator 118 can indicate to a user an amount of charge remaining on a battery of the aerosolization device 100 which powers the functions thereof. The battery indicator may be a digital readout of a charge level or may be a light emitting device, such as an LED, that emits one or more colors of light to indicate a relative state of charge. For example, the battery indicator 118 may emit a single color light to indicate when a charge is low. In other embodiments, the battery indicator 118 may emit three or more colors of light to indicate various levels of charge to show a status of the charge over time.

FIGS. 3A-3K depict embodiments of flow restrictor plates that may be positioned within a conduit, such as conduit 102 of FIGS. 1A and 1B. Restrictor plates, such as restrictor plate 300a, create resistance to and limit airflow through a conduit while adding minimal to no length to a conduit.

The restrictor plate 300a provides an increase in pressure differential that varies with inspiratory flow rates. This pressure differential exists between the conduit and outside of the conduit and/or atmospheric pressure such that as the user's inhalation force increases, the pressure differential drops to maintain a relatively constant flow rate within the conduit that stays in a desired flow rate range. In some embodiments, the pressure differential increases in a linear relationship with the flow rate as the user's inhalation force increases. Sensory feedback provided by sensors and/or indicator mechanisms, such as those described above, may allow the user to relate inspiratory pressure with the required flow rate required to operate the aerosol generator. Restrictor plate 300a defines a plurality of apertures 302a for air to pass through. Apertures 302a can be positioned around an outer periphery of the restrictor plate 300a such that air passing through the apertures forms a relatively laminar flow downstream of the restrictor plate 300a. Apertures 302a can be of any shape or size to create a relatively laminar flow. For example, apertures may be circular and have diameters ranging between about 0.5 mm to 1.5 mm. The size and pattern of the plurality of apertures 302a can prevent airflow through a solid center portion of the restrictor plate 300a, while allowing airflow through the apertures on the periphery thereof.

Figure 3A:
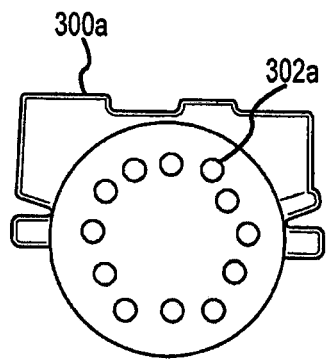
FIGS. 3A-3K illustrate restrictor plates according to embodiments of the invention.
Figure 3B:
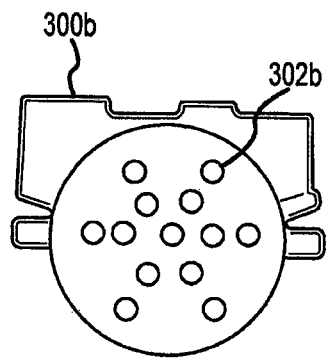
Figure 3C:
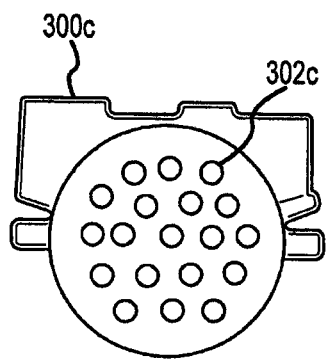
Figure 3D:
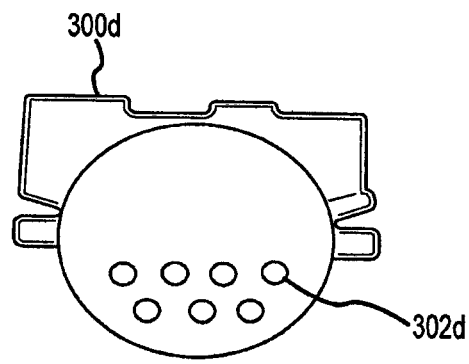
Figure 3E:
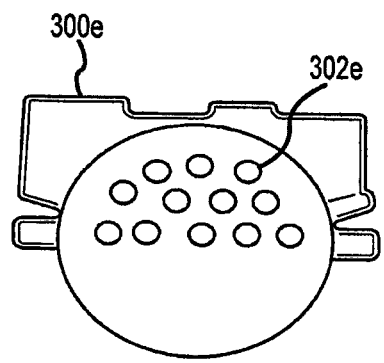
Figure 3F:
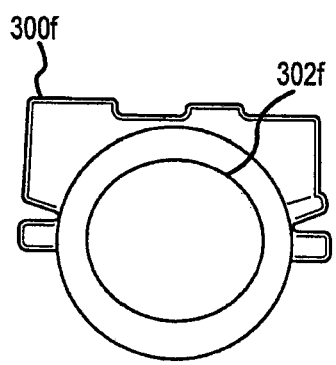
Figure 3G:
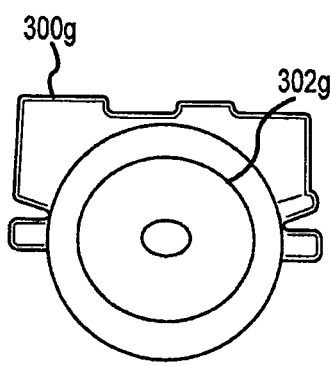
Figure 3H:
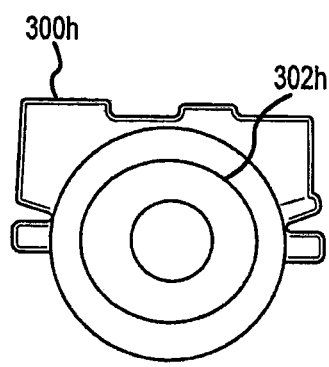
Figure 3I:
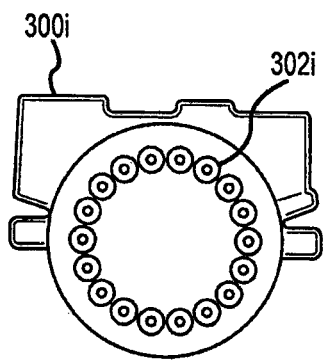
Figure 3J:
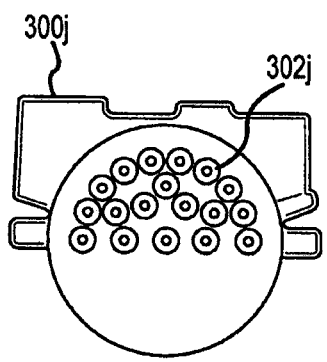
Figure 3K:
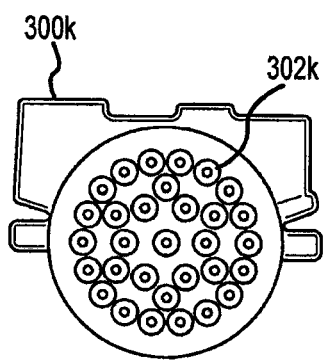

FIGS. 3B-3K show embodiments of restrictor plates defining alternative arrangements of apertures. For example, FIG. 3B shows restrictor plate 300b defining a plurality of apertures 302b arranged in a spoke pattern. FIG. 3C shows a restrictor plate 300c defining a plurality of apertures 302c arranged in a circular pattern. FIG. 3D shows a restrictor plate 300d defining a plurality of apertures 302d arranged in a half circle pattern along a bottom of the restrictor plate 300d. FIG. 3E shows a restrictor plate 300e defining a plurality of apertures 302e arranged in a half circle pattern along a top of the restrictor plate 300e. FIG. 3F shows a restrictor plate 300f defining an aperture 302f that reduces an effective diameter of a conduit. FIG. 3G shows a restrictor plate 300g defining an aperture 302g that reduces an effective diameter of a conduit. FIG. 3H shows a restrictor plate 300h defining an aperture 302h that reduces an effective diameter of a conduit. FIG. 3I shows a restrictor plate 300i defining a tightly grouped plurality of apertures 302i arranged along an outer periphery of the restrictor plate 300i. FIG. 3J shows a restrictor plate 300j defining a plurality of apertures 302j arranged in a half circle pattern along a top half of the restrictor plate 300j. FIG. 3K shows a restrictor plate 300k defining a plurality of apertures 302k arranged in a circular pattern.

Figure 4:
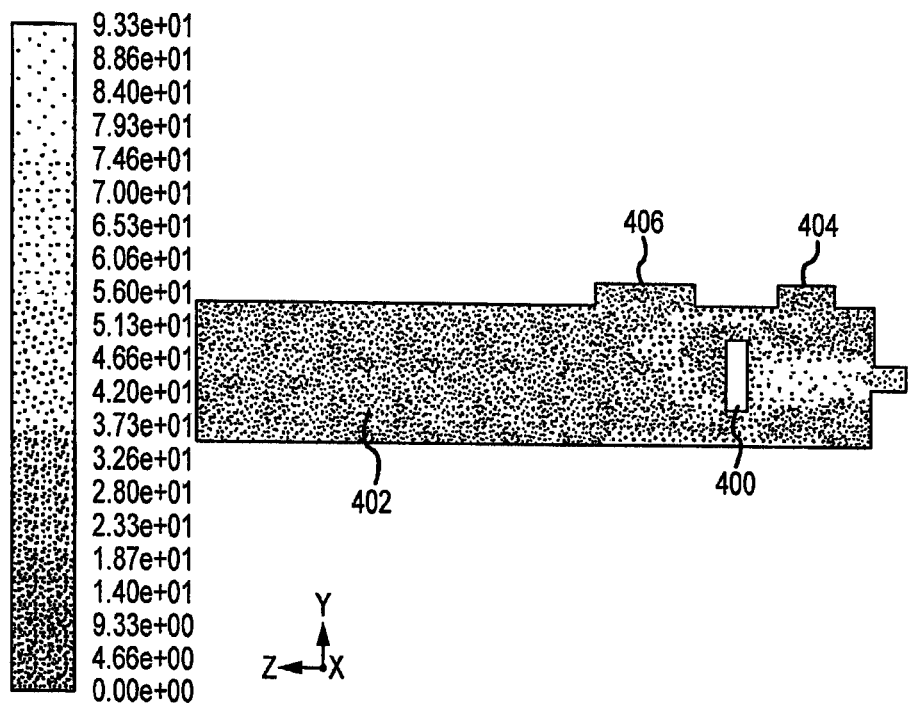
FIG. 4 shows a restrictor plate within a conduit of an aerosolization device according to embodiments of the invention.

FIG. 4 illustrates a restrictor plate 400 positioned within a conduit 402 in accordance with embodiments of the invention. Restrictor plate 400 is disposed within the conduit between a pressure transducer 404 that is in fluid communication with an interior of the conduit and an aerosol generator 406. The pressure transducer 404 monitors a pressure differential within the conduit 402 relative to outside of the conduit and/or atmospheric pressure. A processing unit or IC, such as IC 138 of FIGS. 1A and 1B, may execute software that converts the pressure reading to a flow rate throughout the conduit 402. This flow rate may be used to determine when to activate the aerosol generator 406 to aerosolize a volume of liquid medicament. Restrictor plate 400 may have the characteristics of the restrictor plates 300a-300k discussed above. Restrictor plate 400 creates a laminar flow upstream of the aerosol generator 406 such that the aerosolized medicament is deposited within the laminar flow and entrained within the laminar flow before the aerosolized medicament contacts a wall of the conduit 402 opposite of the aerosol generator 406, in order to maximize the amount of medicament delivered to the user.

Figure 5:
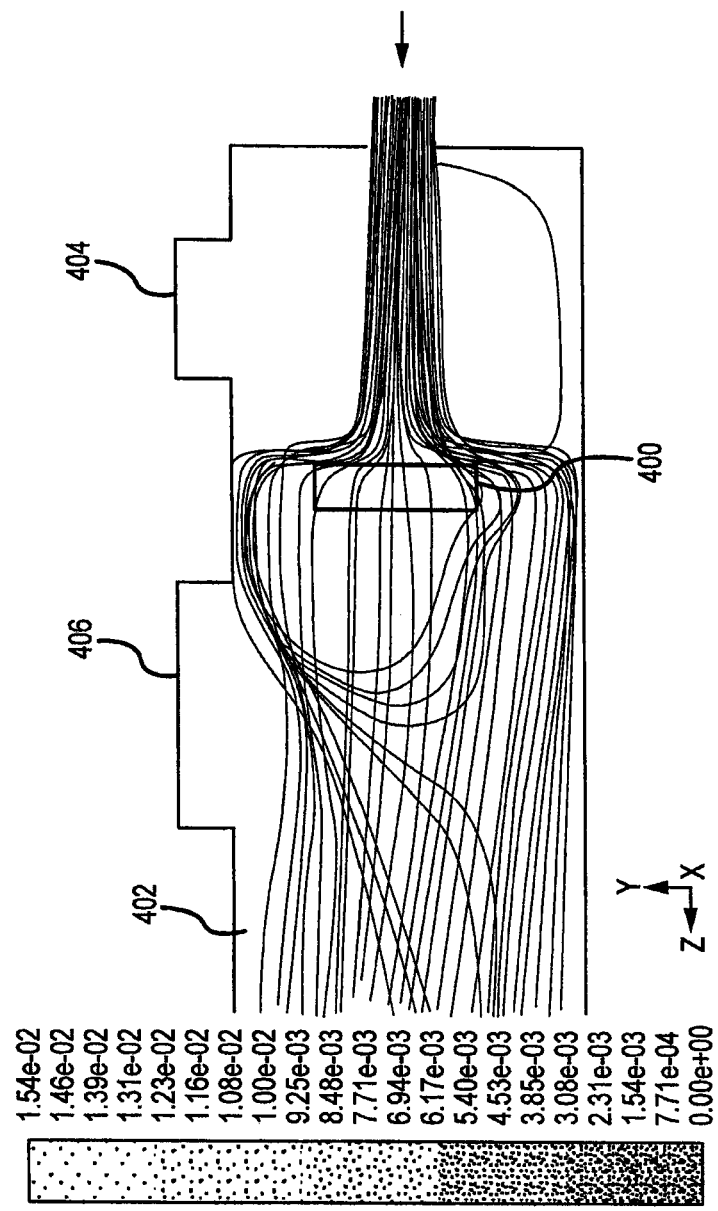
FIGS. 5-7 show laminar flows created by restrictor plates within the conduit of FIG. 4 according to embodiments of the invention.
Figure 6:
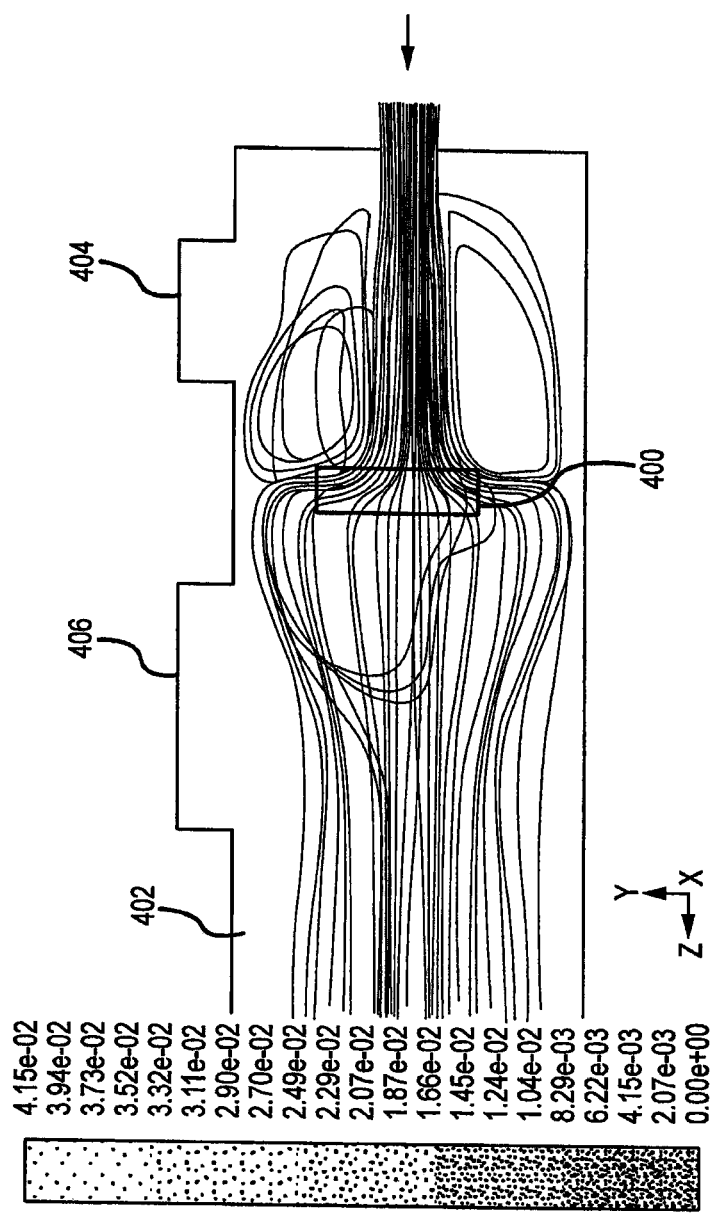
Figure 7:
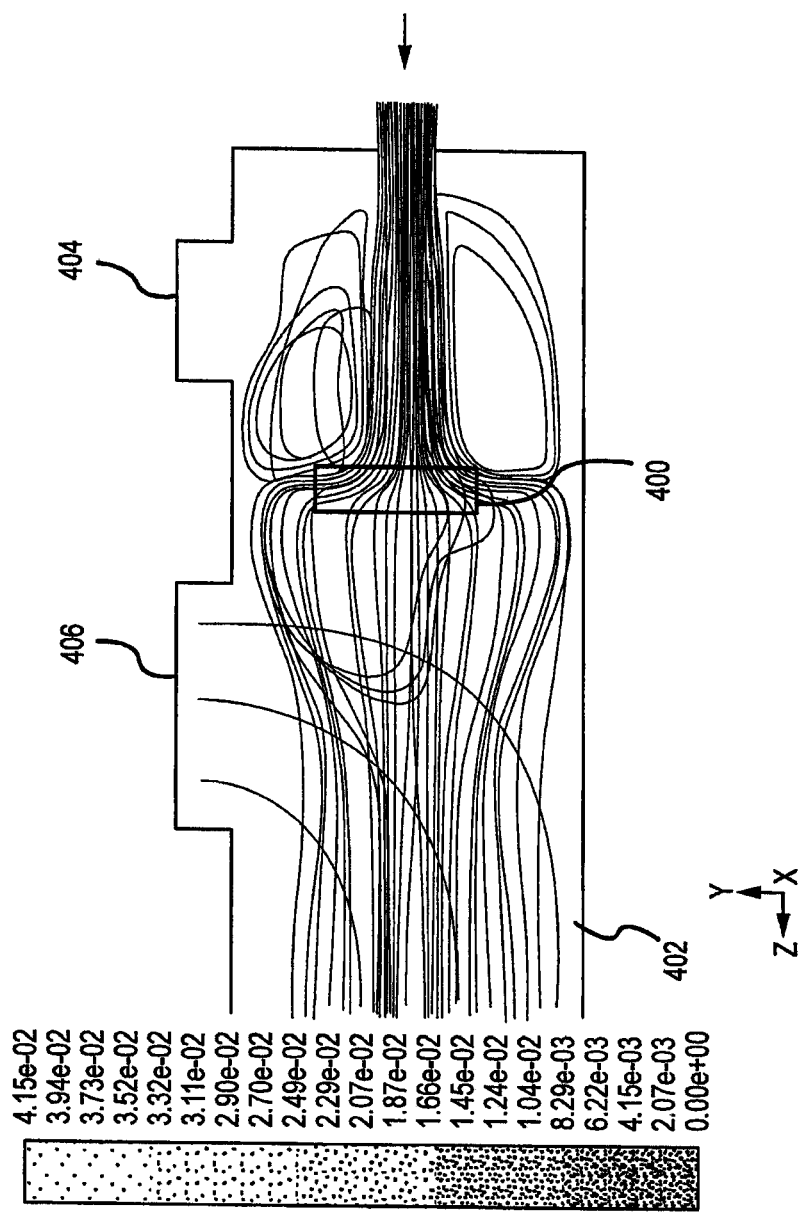

FIGS. 5-7 are laminar flow diagrams of airflow through conduit 402 and restrictor plate 400 having a structure similar to restrictor plate 300a. As airflow reaches restrictor plate 400, the pressure differential is increased and a relatively laminar flow is created to contact aerosolized medicament. The laminar flow provides a consistent velocity field to deliver the aerosolized particles to the user's respiratory system in a consistent manner while minimizing impactive losses. Additionally, the laminar flow minimizes an amount of aerosolized medicament that may be deposited on a wall of the conduit. FIG. 7 shows the laminar flow contacting aerosolized medicament produced by the aerosol generator 406. The aerosolized medicament is entrained in the laminar flow before the medicament contacts a wall opposite of the aerosol generator 406. The entrained aerosolized medicament is then carried out of the conduit 402 to a user's respiratory system.

Figure 8A:
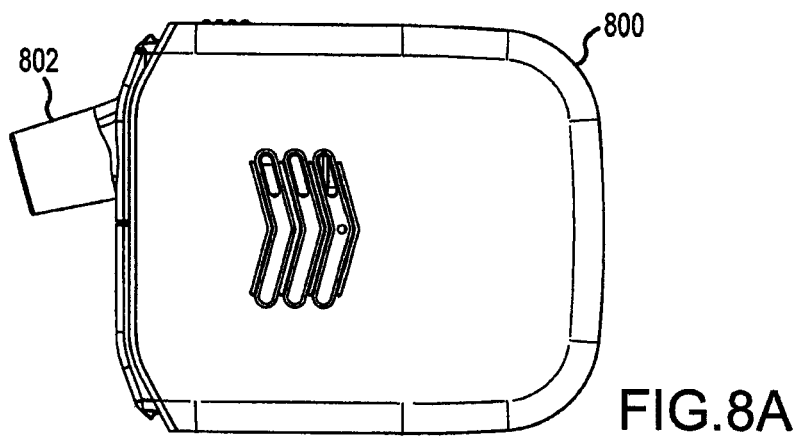
FIGS. 8A-8C depict conduits having mouthpiece ends at various angles according to embodiments of the invention.
Figure 8B:
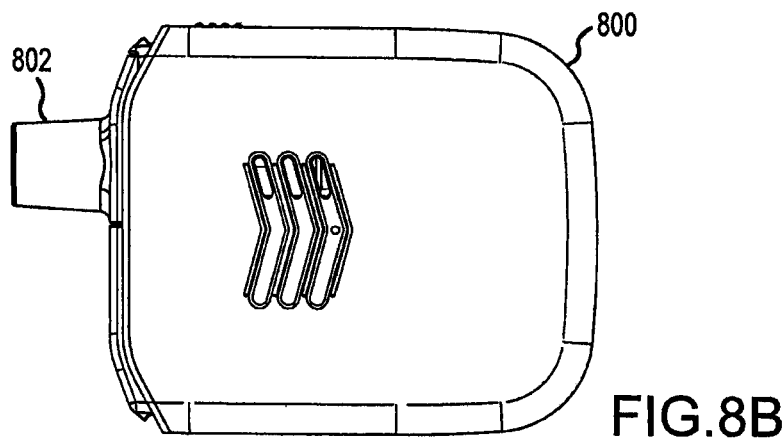
Figure 8C:
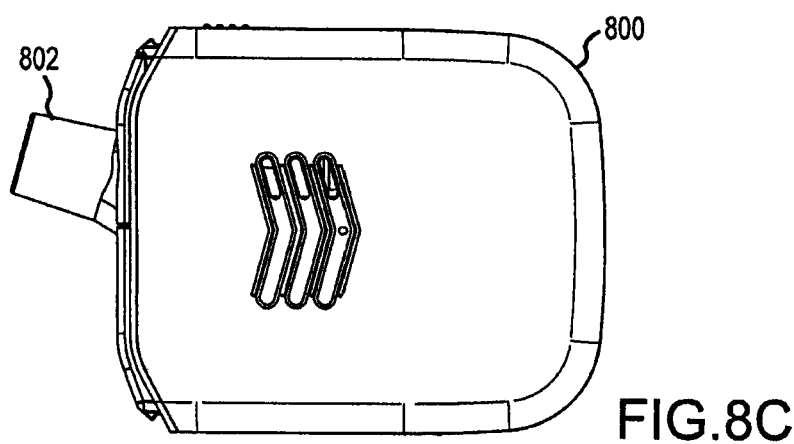

FIGS. 8A-8C show an aerosolization device having a mouthpiece end angled at various angles to direct airflow into a user's respiratory system. Mouthpiece end angles may be set based on the volume of a dose, type of medicament to be delivered, and length and diameter of the conduit of an aerosolization device. FIG. 8A shows an aerosolization device 800 having a mouthpiece end 802 angled downward 15° relative to a horizontal plane. FIG. 8B shows aerosolization device 800 having mouthpiece end 802 parallel relative to a horizontal plane. FIG. 8C shows aerosolization device 800 having mouthpiece end 802 angled upward 15° relative to a horizontal plane. Other angles relative to a horizontal plane of up to 30° up or down relative to a horizontal plane may be used to maximize delivery of the medicament to the user's respiratory system.

Figure 9:
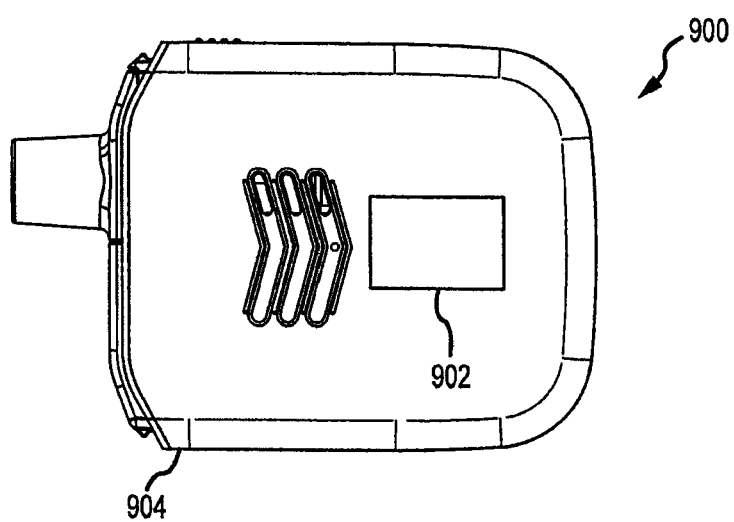
FIG. 9 shows an input device on an aerosolization device according to embodiments of the invention.

FIG. 9 shows an aerosolization device 900 having an input device 902 coupled with a housing 904. In some embodiments, input device 902 may be coupled with a conduit. Input device 902 is configured to receive an input from a user that sets parameters for an inspiratory flow determined by a pressure transducer (not shown) within the conduit. The input may be manually entered by a user, provided via wireless interface, provided via wired interface, such as universal serial bus (USB), or in any other manner. The parameters, which may include a flow rate, an inspiratory pressure, an inspiratory time, and the like, may be used to determine when an aerosol generator of the aerosolization device 900 are actuated, as well as to set ranges for indicator mechanisms (not shown) that direct the user on when and how to breath. An input device 902 may include a keyboard or similar interface, a barcode scanner or RFID reader to receive flow parameters from a user or a container or label of the medicament. Aerosolization device 800 may be configured similar to any of the aerosolization devices described herein, and may include the same or similar features.

Figure 10:
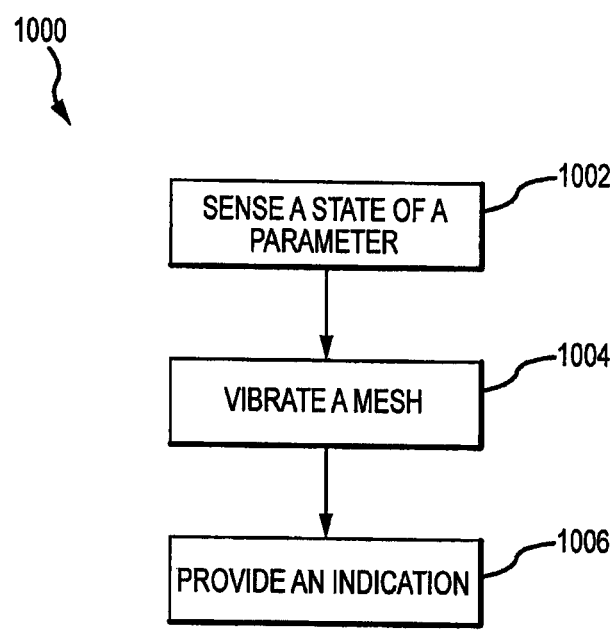
FIG. 10 is a block diagram of a method of using an aerosolization device according to embodiments of the invention.

FIG. 10 depicts a method 1000 of delivering an aerosolized medication to a user's respiratory system using the aerosolization devices described herein. The method may include sensing a state of a flow parameter of an inspiratory flow within a conduit at block 1002. Sensing a state of a flow parameter may be done using sensors, such as a flow sensor or the pressure transducer 404 of FIG. 4. The method may also include vibrating a mesh of an aerosol generator in communication with the conduit to aerosolize a volume of a liquid medicament at block 1004. This vibration produces a plume of aerosolized medicament within a conduit of the aerosolization device when a state of the flow parameter is within a predefined desired range. For example, when an inspiratory flow rate determined by the pressure transducer is within an operating range of the aerosolization device, the mesh may be vibrated. The plume of aerosolized medicament may be provided within a relatively laminar flow produced by a restrictor plate disposed within the conduit upstream of the plume of aerosolized medicament. The laminar flow sweeps the aerosolized medicament toward a mouthpiece end of the conduit before the medicament contacts a wall of the conduit opposite the aerosol generator. The aerosolized medicament is then directed into a user's respiratory system. The method may further include providing an indication using an indicator mechanism coupled with the conduit of the state of the flow parameter relative to the predefined desired range at block 1006.

In some embodiments, providing an indication may include providing a first indication when the flow parameter is within the predefined desired range and providing a second indication when the flow parameter is outside of the predefined desired range. In other embodiments, providing an indication may include providing a first indication when the flow parameter is within the predefined desired range, providing a second indication when the flow parameter is within a predefined secondary range, and providing a third indication when the flow parameter is outside both the predefined desired range and the predefined secondary range.

By indicating the state of the flow parameter within intermediate ranges, a user can alter a rate of inhalation to maximize the efficiency of a delivery of aerosolized medicament. For example, for an aerosol generator having an operating range for a flow rate of between about 5 and 14 L/min, a predefined desired range may be from between about 8 and 11 L/min. A predefined secondary range may be set within the remaining operating range of the aerosol generator. For example, the secondary range may be between about 5 and 7 L/min and between about 12 and 14 L/min. A first indication, such as a green light, may be provided when the flow rate is within the predefined desired range. A second indication, such as a yellow light, may be provided when the flow rate is outside of the desired range but within the secondary range. In other embodiments, a slowly flashing yellow light may be used to indicate that the flow rate is within the lower secondary range and a quickly flashing yellow light can indicate that the flow rate is within the higher secondary range. A third indication, such as a red light, may be used to indicate that flow rate is outside of both the desired range and the secondary range.

Such systems that provide intermediate ranges can help a user correct or otherwise adjust an inhalation rate to maintain a flow rate within a desired or operating range of the aerosolization device before the flow rate is unacceptably inefficient or inoperable to actuate the aerosol generator. This can help a user develop more consistent and efficient inhalations. Multiple intermediate ranges, both within and outside of, the operating range of the aerosol generator may be provided to further aid a user in adjusting the inhalation rate. Additionally, the intermediate ranges may be focused on ensuring that an efficient flow rate range is maintained, rather than ensuring that an operating range of the aerosol generator is maintained.

In some embodiments, the method may further include providing an indication that the liquid medicament is ready to be aerosolized and providing an indication that substantially all of the liquid medicament has been aerosolized. The method may optionally include receiving an input via an input device of the aerosolization device to set the predefined desired range of the flow parameter.

It will be apparent to those skilled in the art that various modifications and variations can be made in the method and system of the present invention without departing from the spirit or scope of the invention. Thus, it is intended that the present invention include modifications and variations that are within the scope of the appended claims and their equivalents.

What is claimed is:

1. An aerosolization device for ensuring proper delivery of an aerosolized medication to a user's respiratory system, the aerosolization device comprising:
    a conduit having a mouthpiece end by which a user may cause an inspiratory flow through the conduit;
    an aerosol generator in communication with the conduit and comprising a vibratable mesh;
    a restrictor disposed within the conduit, wherein the restrictor defines a plurality of apertures disposed along an outer periphery of the restrictor, the plurality of apertures being configured to:
    provide an increase in pressure differential that varies with an inspiratory flow rate within the conduit; and
    provide a relatively laminar flow downstream of the restrictor compared to upstream of the restrictor; and
    an indicator mechanism that indicates to a user a state of a parameter of the inspiratory flow relative to a predefined desired range, wherein indicating to the user the state of the parameter of the inspiratory flow relative to the predefined desired range comprises:
    the indicator mechanism providing a first indication when the parameter of the inspiratory flow is within the predefined desired range;
    the indicator mechanism providing a second indication when the parameter of the inspiratory flow is within a predefined secondary range, wherein the predefined secondary range extends above and below the predefined desired range and is within an operating range of the aerosol generator; and
    the indicator mechanism providing a third indication when the parameter of the inspiratory flow is outside of both the predefined desired range and the predefined secondary range.

2. The aerosolization device for ensuring proper delivery of an aerosolized medication to a user's respiratory system according to claim 1, wherein the indicator mechanism comprises:
    at least one selection from a group consisting of a light, a digital readout, a speaker, or a vibration-generating device.

3. The aerosolization device for ensuring proper delivery of an aerosolized medication to a user's respiratory system according to claim 1, wherein the parameter of the inspiratory flow comprises:
    the inspiratory flow rate within the conduit.

4. The aerosolization device for ensuring proper delivery of an aerosolized medication to a user's respiratory system according to claim 3, wherein:
    the predefined desired range of the inspiratory flow rate is between 5 and 14 liters per minute (L/min).

5. The aerosolization device for ensuring proper delivery of an aerosolized medication to a user's respiratory system according to claim 1, the aerosolization device further comprising:
an input device for receiving and setting the predefined desired range of the parameter of the inspiratory flow.

6. The aerosolization device for ensuring proper delivery of an aerosolized medication to a user's respiratory system according to claim 1, wherein:
the restrictor is configured such that fluid only flows through the plurality of apertures disposed along the outer periphery.

7. An aerosolization device for ensuring proper delivery of an aerosolized medication to a user's respiratory system, the aerosolization device comprising:
a conduit having a mouthpiece end by which a user may cause an inspiratory flow through the conduit;
an aerosol generator in communication with the conduit and comprising a vibratable mesh;
a restrictor disposed within the conduit, wherein the restrictor defines a plurality of apertures disposed along an outer periphery of the restrictor, the plurality of apertures being configured to:
provide an increase in pressure differential that varies with an inspiratory flow rate within the conduit; and
provide a relatively laminar flow downstream of the restrictor compared to upstream of the restrictor; and
an indicator mechanism that indicates to a user a state of a parameter of the inspiratory flow relative to a predefined desired range, wherein indicating to the user the state of the parameter of the inspiratory flow relative to the predefined desired range comprises:
the indicator mechanism providing a first indication when the parameter of the inspiratory flow is within the predefined desired range;
the indicator mechanism providing a second indication when the parameter of the inspiratory flow is within a predefined secondary range, wherein the predefined secondary range extends above and below the predefined desired range and is within an operating range of the aerosol generator; and
the indicator mechanism providing a third indication when the parameter of the inspiratory flow is outside of both the predefined desired range and the predefined secondary range,
wherein the vibratable mesh produces a plume of aerosolized medicament within the relatively laminar flow when the inspiratory flow rate is within an operating range of the aerosol device.

8. The aerosolization device for ensuring proper delivery of an aerosolized medication to a user's respiratory system according to claim 7, wherein:
the restrictor is configured such that fluid only flows through the plurality of apertures disposed along the outer periphery.

9. The aerosolization device for ensuring proper delivery of an aerosolized medication to a user's respiratory system according to claim 8, wherein the parameter of the inspiratory flow comprises:
the inspiratory flow rate, and the predefined desired range is the operating range of the inspiratory flow rate.

10. The aerosolization device for ensuring proper delivery of an aerosolized medication to a user's respiratory system according to claim 7, wherein:
the operating range of the inspiratory flow rate is between 5 and 14 L/min.

11. A method of delivering an aerosolized medication to a user's respiratory system, the method comprising:
sensing a state of a flow parameter of an inspiratory flow within a conduit, the conduit having a mouthpiece end by which a user may cause the inspiratory flow within the conduit;
providing an indication using an indicator mechanism of the state of the flow parameter relative to a predefined desired range, wherein providing an indication comprises:
providing a first indication when the flow parameter is within the predefined desired range;
providing a second indication when the flow parameter is within a predefined secondary range, wherein the predefined secondary range extends above and below the predefined desired range and is within an operating range of an aerosol generator; and
providing a third indication when the flow parameter is outside both the predefined desired range and the predefined secondary range; and
vibrating a mesh of the aerosol generator in communication with the conduit to aerosolize a volume of a liquid medicament to produce a plume of aerosolized medicament within the conduit when the state of the flow parameter is within a predefined desired range, wherein:
the plume of aerosolized medicament is provided within a relatively laminar flow produced by a restrictor disposed within the conduit upstream of the plume of aerosolized medicament;
the restrictor defines a plurality of apertures disposed around an outer periphery of the restrictor; and
the plume of aerosolized medicament is carried by the relatively laminar flow toward the mouthpiece end of the conduit.

12. The method of delivering an aerosolized medicament to a user's respiratory system according to claim 11, wherein:
the predefined desired range is between 5 and 14 L/min.

13. The method of delivering an aerosolized medicament to a user's respiratory system according to claim 11, the method further comprising:
providing an indication that the liquid medicament is ready to be aerosolized; and
providing an indication that substantially all of the liquid medicament has been aerosolized.

14. The method of delivering an aerosolized medicament to a user's respiratory system according to claim 11, the method further comprising:
receiving an input to set the predefined desired range of the flow parameter.

* * * * *